United States Patent
Maier et al.

[11] Patent Number: 5,981,437
[45] Date of Patent: Nov. 9, 1999

[54] HERBICIDAL SUBSTITUTED PYRIDINE COMPOUNDS

[75] Inventors: Thomas Maier; Stefan Scheiblich, both of Mainz; Helmut Siegfried Baltruschat, Schweppenhausen, all of Germany; Joseph Luke Pont, Lawrenceville, N.J.

[73] Assignee: American Cyanamid Company, Madison, N.J.

[21] Appl. No.: 08/889,863

[22] Filed: Jul. 8, 1997

Related U.S. Application Data

[60] Provisional application No. 60/023,134, Jul. 30, 1996.
[51] Int. Cl.$^6$ .................... C07D 213/69; C07D 213/270; C07D 401/04; A01N 43/40
[52] U.S. Cl. .................... 504/244; 546/275.4; 546/256; 546/261; 546/280.4; 546/296
[58] Field of Search .................... 546/275.4; 504/244

[56] References Cited

FOREIGN PATENT DOCUMENTS

| | | |
|---|---|---|
| 0 572 093 | 12/1993 | European Pat. Off. . |
| 0 692 474 | 1/1996 | European Pat. Off. . |
| 0 693 490 | 1/1996 | European Pat. Off. . |
| 0 694 538 | 1/1996 | European Pat. Off. . |
| WO94/22833 | 10/1994 | WIPO . |

*Primary Examiner*—Alan L. Rotman
*Attorney, Agent, or Firm*—Joseph M. Mazzarese

[57] ABSTRACT

The novel compounds of formula I:

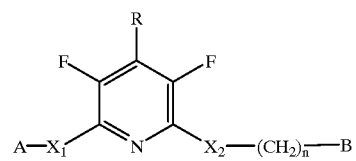

(I)

wherein
  A represents an optionally substituted 5- or 6-membered heteroaromatic group or an optionally substituted aryl group or a difluorobenzodioxolyl group;
  B represents an optionally substituted cyclic hydrocarbon or thienyl, an alkyl, alkenyl or alkynyl group or independently has one of the meanings of A;
  n represents an integer from 0 to 2;
  R represents a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino or alkoxyamino group or a formamidino or cyano group;
  $X_1$ and $X_2$ independently represent an oxygen or sulphur atom, and the herbicidal use of these compounds.

10 Claims, No Drawings

HERBICIDAL SUBSTITUTED PYRIDINE COMPOUNDS

This application claims priority from copending provisional application(s) Ser. No. 60/023,134 filed on Jul. 30, 1996.

BACKGROUND OF THE INVENTION

Selective herbicidal compounds play an important role in agriculture and related fields. Growers seek herbicides that kill pest plants, but do not reduce crop yield. Although numerous selective herbicides have been described, there is nevertheless a considerable interest in new compounds having a superior or different activities, because the known herbicidal compounds either are not suitable for application in certain crops, or are not sufficiently selective.

Selective herbicides the active ingredients of which are pyrindine derivatives, and particularly 2,6-substituted pyridines, are known from EP0570293, EP0692474, EP0693490 and WO 94/22833. However, 2,6-disubstituted pyridine derivatives containing two or three additional substituents have not yet been described.

SUMMARY OF THE INVENTION

The present invention provides novel tetra- and pentasubstituted pyridines of formula I:

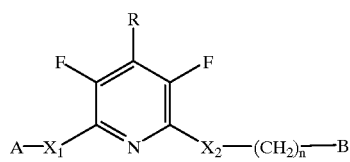

(I)

wherein
- A represents an optionally substituted 5- or 6-membered heteroaromatic group or an optionally substituted aryl group or a difluorobenzodioxolyl group;
- B represents an optionally substituted cyclic hydrocarbon, an alkyl, alkenyl or alkynyl group or independently has one of the meanings of A;
- n represents an integer from 0 to 2;
- R represents a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino or alkoxyamino group or a formamidino or cyano group;
- $X_1$ and $X_2$ independently represent an oxygen or sulphur atom;

the new compounds show an excellent selective herbicidal activity in various crops.

It is an object of the present invention to provide novel, selective herbicidal compounds.

It is also an object of the invention to provide methods for controlling undesired plant growth by contacting said plants with a herbicidally effective amount of the new compounds.

It is another object of the invention to provide selective herbicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the novel tetra- and pentasubstituted pyridines of formula I:

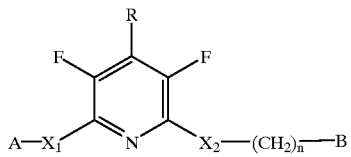

(I)

wherein A, B, R, n, $X_1$, and $X_2$ are as described above, show considerable herbicidal activity and high selectivity in certain crops, such as maize and rice, in pre- and post-emergence applications on both broadleaf and grassy weed species.

In the definitions of the new compounds, an aryl group is suitably an optionally substituted phenyl or naphthyl group. Within the definition of A, the 5- or 6-membered heteroaryl group comprises optionally substituted 5- or 6-membered heterocycles containing one or more nitrogen and/or oxygen and/or sulphur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. A also includes bicyclic systems which consist of a benzene ring fused with a 5- or 6-membered heterocyclic ring as defined above. Another preferred embodiment of A is a difluorobenzodioxolyl group of formula

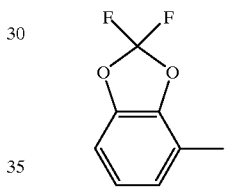

Generally, in compounds of the present invention, alkyl, alkenyl or alkynyl groups, unless otherwise specified, may be linear or branched and may contain up to 12, preferably up to 6, and most preferably up to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, alkylthio, haloalkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl, haloalkylthio and haloalkoxy are preferably mono-, di- or trifluoroalkyl, -alkylthio and -alkoxy, especially trifluoromethyl, difluoromethoxy, trifluoromethylthio, difluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, haloalkylthio, alkylamino and dialkylamino groups, specific examples of such substituents include phenyl, halogen atoms, nitro, cyano, hydroxyl, $C_{1-4}$-alkoxy, $C_{1-4}$-haloalkoxy, $C_{1-4}$-haloalkylthio and $C_{1-4}$-alkoxycarbonyl groups.

In relation to moieties defined above as comprising an optionally substituted aryl or heteroaryl group, optional substituents include halogen, nitro, cyano, amino, hydroxyl, $C_{1-4}$-alkyl, $C_{1-4}$-alkoxy, $C_{1-4}$-haloalkyl, $C_{1-4}$-haloalkylthio, $C_{1-4}$-haloalkoxy, $C_{2-4}$ haloalkenyl, and halosulfanyl groups having 1–5 halogen atoms, such as $SF_5$. From 1 to 5 substituents may be present, 1 to 2 substituents being preferred. Typically, haloalkyl, haloalkoxy and haloalkylthio groups are trifluoromethyl, difluoromethoxy, trifluoromethoxy, difluoromethylthio and trifluoromethylthio groups.

Preferred compounds within the above definitions are those in which A represents a phenyl, pyridyl or pyrazolyl group, unsubstituted or substituted by one or more identical or different substituents selected from halogen atoms, alkyl, alkoxy, haloalkyl, haloalkylthio, haloalkoxy and pentahalosulfanyl groups.

In formula I A preferably represents a group of formula a, b or c:

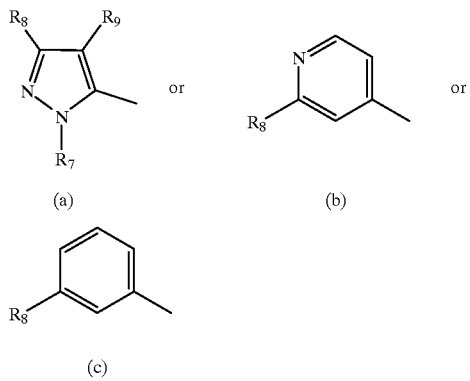

wherein $R_9$ is hydrogen, fluoro or chloro; $R_7$ is $C_{1-3}$ alkyl and $R_8$ is $C_{1-4}$ alkyl, $C_{1-3}$ haloalkyl, a halogen atom, or $C_{1-3}$-haloalkylthio or $C_{1-3}$ haloalkoxy; while the group —$X_2$—$(CH_2)_n$—B preferably has one of the meanings of A—$X_1$— or particularly represents a—$X_2$—$CH_2$-thienyl, -halothienyl, -alkylthienyl, -haloalkylthienyl, -alkoxythienyl, -haloalkylthiothienyl, -haloalkoxythienyl, —$SF_5$— thienyl, an unsubstituted or a 1–5fold substituted —$X_2$—$(CH_2)_n$-phenyl group wherein the substituents independently are alkyl, haloalkyl, alkoxy, haloalkoxy, cyano or $SF_2$ groups or halogen atoms.

If not otherwise defined, the index n is preferably 0 or 1, $X_1$ and $X_2$ are preferably oxygen atoms.

Particularly preferred are those compounds of formula I, wherein A represents one of the groups a', b' or c':

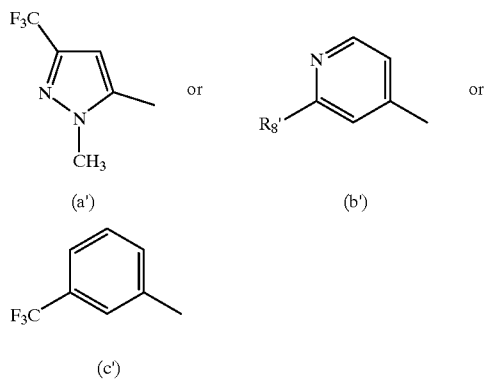

where $R_8'$ is a chlorine atom, a trifluoromethyl or a difluoromethoxy group, and R is a methyl, ethyl, methoxy, methylthio, methylamino group or a hydrogen, fluorine, bromine or chlorine atom.

Most preferably R is methyl or methoxy, and A is a' or c'.

When n is 0, B preferably represents a group within the meaning of A, an unsubstituted phenyl group or a phenyl group substituted by 1 to 3 substituents independently selected from the group comprising fluorine and chlorine atoms and haloalkyl and haloalkoxy groups, especially fluorophenyls or 3-trifluoromethylphenyls.

If n is 1, then B preferably represents a phenyl group substituted by 1 to 3 substituents independently selected from the group consisting of alkyl and haloalkyl groups and fluorine and chlorine atoms; or B represents a thien-2-yl or thien-3-yl group which may be substituted by one or two substituents independently selected from the group consisting of fluorine and chlorine atoms and alkyl and haloalkyl groups, e.g., methyl or trifluoromethyl groups. Examples for the substituted thienyl groups are 5-fluoro-, 5-chloro- and 5-trifluoromethylthien-2-yl or -3-yl.

The compounds of this invention can be prepared according to known methods, particularly as follows:

(A) For the preparation of compounds of formula I, wherein R represents alkoxy, alkoxyalkoxy, alkylthio, amino, alkylamino, dialkylamino, alkoxyamino or cyano, a compound of formula II:

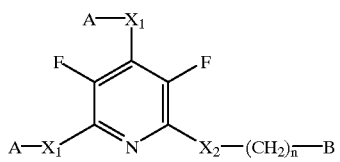

(II)

where A, B, n, $X_1$ and $X_2$ are defined as above, is reacted with an equimolar amount or an excess of a compound of formula III:

R—H     (III)

wherein R is alkoxy, alkoxyalkoxy, alkylthio, amino, alkylamino, dialkylamino, alkoxyamino or cyano, or a metal salt thereof, under basic conditions.

(B) For the preparation of compounds of formula I, wherein the group $X_2$—$(CH_2)_n$—B is identical with A—$X_1$—, a compound of formula IV:

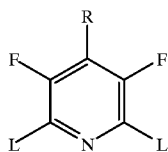

(IV)

wherein R is defined as above, and L are independently leaving groups, is reacted with at least a twofold excess of a compound of formula V:

(V)

wherein A and $X_1$ are defined as above, or a metal salt thereof, under basic conditions.

Throughout this specification, suitable leaving groups, L, include alkyl- or arylsulfonyl groups, alkyl- or arylsulfonyloxy groups, perfluoroalkylsulfonyl or perfluoroalkylsulfonyloxy groups, nitro, halogen (e.g., fluorine, chlorine and bromine), and the like.

(C) A compound of formula VI:

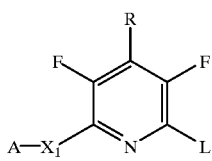

(VI)

(wherein A, L, R and $X_1$ are defined as above) is reacted with a compound of formula VII:

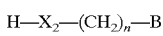

(VII)

(wherein B, n and $X_2$ are defined as above) or a metal salt thereof under basic conditions.

(D) A compound of formula VIII:

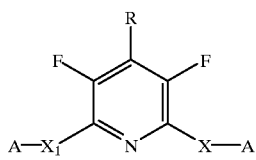

(VIII)

(wherein A, R and $X_1$ are defined as above) is reacted with an equimolar amount of a compound of formula VII or a metal salt thereof under basic conditions.

(E) A compound of formula IX:

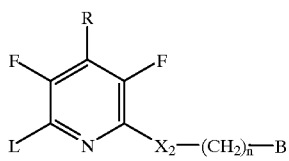

(IX)

(wherein B, L, R, n and $X_2$ are defined as above) is reacted with an equimolar amount of a compound of formula V or a metal salt thereof under basic conditions.

(F) For the preparation of compounds of formula I, wherein R is a halogen atom or a cyano group, the amino group in a compound of formula X:

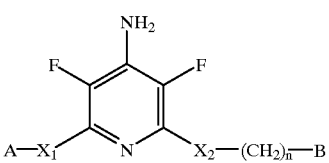

(X)

is diazotated and the diazonium group is replaced by halogen or cyano.

(G) For the preparation of compounds of formula I, wherein R is a formamidino group, a compound of formula X is reacted with a suitable formic acid derivative.

The reactions A to E and G are conveniently carried out in an organic solvent at elevated temperature. Generally, any polar organic solvent is suitable, e.g. dimethylformamide, tetrahydrofuran, sulfolane, pyridines. The metal salts of the A—$X_1$—H compounds, the alcohols and thiols are suitably alkali metal salts, preferably the sodium or potassium salts. In some cases, the presence of copper salts has been found to be useful.

Reaction F may be carried out in an aqueous medium and the diazonium compound can be reacted e. g. with CuCl, CuBr, CuCN or KI to introduce the chlorine, bromine, iodine atom or the cyano group.

The metal salts are conveniently generated by reaction of the A—$X_1$—H or B—$(CH2)_n$—$X_2$—H compounds, the alcohols or thiols with a suitable metal base, a metal carbonate or hydride.

The prepared compounds of formula I may be isolated and purified using conventional methods and techniques.

The starting compounds for the preparation of compounds of this invention can be prepared according to known methods. Pyridine compounds of formulae II, IV, VI, VIII and IX may be synthesized starting from pentafluoropyridine, wherein the fluorine atoms in the 2, 4 and 6 positions can be replaced, e.g., by groups of formula A—$X_1$, which in turn can be replaced stepwise by a suitable group R and a group $X_2$—$(CH_2)_n$—B.

The present invention also extends to herbicidal compositions which comprise a compound of formula I and at least one agronomically acceptable carrier.

Preferably there are at least two such carriers combined with a compound of formula I in a composition according to the present invention, at least one of which is a surface-active agent.

A carrier in a composition according to the invention is any material with which the active ingredient is formulated to facilitate application to the locus to be treated, which locus may be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kacilinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic, hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythrol; condensates of these with ethylene oxide and/or propylene oxide; condensation products of fatty alcohol or alkyl phenols, for example P-octylphenol or p-octylcresol, with ethylene oxide and/or propylene oxide; sulphates or sulphonates of these condensation products; alkali or earth alkali metal salts, preferably sodium salts; sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

A herbicidal composition of the invention may also contain other active ingredients, for example, compounds possessing insecticidal or fungicidal properties, or other herbicides.

An example of a general formulation according to the invention is 100 g of active ingredient (compound of formula 1), 30 g of dispersing agent, 3 g of antifoaming agent, 2 g of structure agent, 50 g of anti-freezing agent, 0.5 g of a biocidal agent and sufficient water to make 1000 ml. Prior to use it is diluted with water to give the desired concentration of active ingredient.

Formulations are applied at a dosage that provides a herbicidally effective amount of the compound of the invention. The compounds of formula I are typically applied in a dose of about 0.005 to 1, preferably 0.01 to 0.5 kg/ha. The amount to be used depends mainly on the kind of active ingredient, the formulation, the climatic conditions and the weeds to be controlled. Also, the resistance of the crops has to be taken into consideration.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLE 1

(a) 3,5-Difluoro-2.4.6-tris(1-methyl-3-trifluoromethylpyrazol-5-yloxy)pyridine

A mixture of pentafluoropyridine (16.9 g, 0.1 mol), 5-hydroxy-1-methyl-3-trifluoromethylpyrazole (potassium salt, 62 g, 0.33 mol), and potassium carbonate (45.5 g, 0.33 mol) in anhydrous sulfolane (70 ml) is heated to 80° C. for 4 hours and then to 100° C. for 3 hours. The reaction mixture is diluted with pentane/ethyl acetate (1/1 by volume). After filtration through a bed of silica gel the filtrate is washed 8 times with water. The organic layer is dried with anhydrous magnesium sulfate and filtered over silica gel. Now the solvent is removed and the residue is washed with diisopropyl ether. After drying, colorless crystals (39.1 g, 64% yield) of melting point 119° C. are obtained.

(b) Preparation of 2.6-Bis(1-methyl-3-trifluoromethylpyrazol-5-yloxy)-3.5-difluoro-4-methoxypyridine A 25% solution of potassium methylate in dry methanol (4.4 ml, 15 mmol) is added to a solution of 3,5-difluoro-2, 4,6-tris (1-methyl-3-trifluoromethylpyrazol-5-yloxy) pyridine (9.1 g, 15 mmol; see (a) above) in dry methanol (50 ml). After 30 min at ambient temperature the reaction is stopped by adding 2 ml of water. The solvent is removed under reduced pressure and pentane/ethyl acetate (1/1 by volume) is added to the residue. After filtration through a bed of silica gel the filtrate is washed with a 2 N sodium hydroxide solution. After drying and filtration of the organic layer, the solvents are removed and the residue is washed with diisopropyl ether. One obtains colorless crystals (5.3 g 75% yield), m.p. 83° C.

EXAMPLE 2

2,6-Bis(1-methyl-3-trifluoromethylpyrazol-5-yloxy)-3.5-difluoro-4-methylpyridine and 2-(1-Methyl-3-trifluoromethylpyrazol-5-yloxy)-4-methyl-3.5.6-trifluoropyridine A mixture of 4-methyl-2,3,5,6-tetrafluoropyridine (4 g, 24 mmol), potassium carbonate (3.7 g, 26.5 mmol) and 5-hydroxy-1-methyl-3-trifluoromethylpyrazole (4.4 g, 26.5 mmol) in anhydrous DMF (20 ml) is heated to 80° C. overnight. After cooling, the solvent is removed under reduced pressure. Pentane/ethyl acetate (1/2 by volume) is added to the residue and the mixture is washed twice with water. After drying of the organic layer, the solvent is removed and both products are purified by flash chromatography: One obtains 2-(1-methyl-3-trifluoromethylpyrazol.-5-yloxy)-4-methyl-3,5,6-trifluoropyridine (silica gel, pentane/ethyl acetate 1/1 by volume) (1.6 g, 21%) and 2,6-bis(1-methyl-3-trifluoromethylpyrazol-5-yloxy)-3,5-difluoro-4-methylpyridine (silica gel, pentane/ethyl acetate 1/1) (4.8 g, 43% yield, m.p. 101° C.).

EXAMPLE 3

3,5-Difluoro-6-(3,4-difluorophenoxy)-4-methyl-2-(1-methyl-3-trifluoromethylpyrazol-5-yloxy)pyridine A mixture of 2-(1-methyl-3-trifluoromethylpyrazol-5-yloxy)-4-methyl-3,5,6-trifluoropyridine (1.2 g, 4 mmol; see Example 2), 60% sodium hydride (0.2 g, 4 mmol) and 3,4-difluorophenol (0.65 g, 5 mmol) in anhydrous sulfolane (5 ml) is heated to 90° C. overnight. The reaction mixture is diluted with pentane/ethyl acetate (1/1 by volume) and filtered through a bed of silica gel. The filtrate is washed 8 times with water, the organic layer is dried with anhydrous magnesium sulfate, and the solvents are removed in vacuo. The residue is purified by a flash silica gel chromatography using pentane/ethyl acetate in a ratio of 9/1. 0.9 g (53% yield) of the title compound are obtained as a colourless solid, m.p. 93° C.

EXAMPLE 4

3,5-Difluoro-4-methoxy-2-(1-methyl-3-trifluoromethylpyrazol-5-yloxy)-6-(2-methylbenzyloxy)pyridime Sodium hydride (0.1 g, 60%, 2.5 mmol) is added to a solution of 2-methylbenzyl alcohol (0.3 g, 2.5 mmol) in sulfolane (5 ml) at 50° C. After 1 hour at 50° C. 2,6-bis(1-methyl-3-trifluoromethylpyrazol-5-yloxy)-3,5-difluoro-4-methoxypyridine (1.1 g, 2.3 mmol; see Example 1(b)) is added to the reaction mixture. The mixture is heated to 90° C. for 2 hours. After cooling, the reaction mixture is diluted with pentanelethyl acetate (1/1 by volume) and filtered through a bed of silica gel. The filtrate is washed 6 times with water. The organic layer is dried with anhydrous magnesium sulfate, filtered and the solvents evaporate in vacuo. Purification by flash chromatography (2 times: silica gel, pentane/ethyl acetate 8/2 v/v and silica gel: toluene) gives the title compound (0.15 g, 15% yield) of melting point 44° C.

EXAMPLE 5

The compounds listed in the TABLES 1 and 3 can be prepared by methods analogeous to those described in examples 1 to 4, and according to the methods described in the foregoing description.

TABLE 1

Compounds of formula

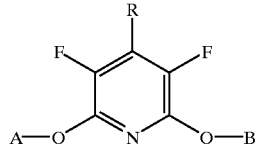

(Ia)

| Compound No. | A | B | R | m.p. [° C.] |
|---|---|---|---|---|
| 1 | 1-CH$_3$-3-CF$_3$-pyrazol-5-yl | 1-CH$_3$-3-CF$_3$-pyrazol-5-yl | Me | 101 |
| 2 | 1-CH$_3$-3-CF$_3$-pyrazol-5-yl | 3,4-di-F-phenyl | Me | 93 |
| 3 | 1-CH$_3$-3-CF$_3$-pyrazol-5-yl | 1-CH$_3$-3-CF$_3$-pyrazol-5-yl | Me | 93 |
| 4 | 1-CH$_3$-3-CF$_3$-pyrazol-5-yl | 3-F-phenyl | Me | |
| 5 | 1-CH$_3$-3-CF$_3$-pyrazol-5-yl | 3-CF$_3$-4-Cl-phenyl | Me | |
| 6 | 1-CH$_3$-3-CF$_3$-pyrazol-5-yl | 3-Cl-4-F-phenyl | Me | |
| 7 | 1-CH$_3$-3-CF$_3$-pyrazol-5-yl | 3-CF$_3$-4-F-phenyl | Me | |
| 8 | 1-CH$_3$-3-CF$_3$-pyrazol-5-yl | 3,4-di-Cl-phenyl | Me | |
| 9 | 1-CH$_3$-3-CF$_3$-pyrazol-5-yl | 3,5-di-F-phenyl | Me | |
| 10 | 1-CH$_3$-3-CF$_3$-pyrazol-5-yl | 3,4-di-F-phenyl | MeO | |
| 11 | 1-CH$_3$-3-CF$_3$-pyrazol-5-yl | 3-F-phenyl | MeO | |
| 12 | 1-CH$_3$-3-CF$_3$-pyrazol-5-yl | 3-CF$_3$-4-Cl-phenyl | MeO | |
| 13 | 1-CH$_3$-3-CF$_3$-pyrazol-5-yl | 3-Cl-4-F-phenyl | MeO | |
| 14 | 1-CH$_3$-3-CF$_3$-pyrazol-5-yl | 3-CF$_3$-4-F-phenyl | MeO | |
| 15 | 1-CH$_3$-3-CF$_3$-pyrazol-5-yl | 3,4-di-Cl-phenyl | MeO | |
| 16 | 1-CH$_3$-3-CF$_3$-pyrazol-5-yl | 3,5-di-F-phenyl | MeO | |
| 17 | 3-CF$_3$-phenyl | 3-CF$_3$-phenyl | MeO | |
| 18 | 3-CF$_3$-phenyl | 3,4-di-F-phenyl | MeO | |
| 19 | 3-CF$_3$-phenyl | 3-F-phenyl | MeO | |
| 20 | 3-CF$_3$-phenyl | 3-CF$_3$-4-Cl-phenyl | MeO | |
| 21 | 3-CF$_3$-phenyl | 3-Cl-4-F-phenyl | MeO | |
| 22 | 3-CF$_3$-phenyl | 3-CF$_3$-4-F-phenyl | MeO | |
| 23 | 3-CF$_3$-phenyl | 3,4-di-Cl-phenyl | MeO | |
| 24 | 3-CF$_3$-phenyl | 3,5-di-F-phenyl | MeO | |
| 25 | 3-CF$_3$-phenyl | 3-CF$_3$-phenyl | Me | |
| 26 | 3-CF$_3$-phenyl | 3,4-di-F-phenyl | Me | |
| 27 | 3-CF$_3$-phenyl | 3-F-phenyl | Me | |
| 28 | 3-CF$_3$-phenyl | 3-Cl-4-F-phenyl | Me | |
| 29 | 2-Cl-pyrid-4-yl | 2-Cl-pyrid-4-yl | Me | |
| 30 | 2-Cl-pyrid-4-yl | 3-CF$_3$-phenyl | Me | |
| 31 | 2-Cl-pyrid-4-yl | 3,4-di-F-phenyl | Me | |
| 32 | 2-Cl-pyrid-4-yl | 3-F-phenyl | Me | |
| 33 | 2-Cl-pyrid-4-yl | 3-Cl-4-F-phenyl | Me | |
| 34 | 2-Cl-pyrid-4-yl | 2-Cl-pyrid-4-yl | MeO | |
| 35 | 2-Cl-pyrid-4-yl | 3-CF$_3$-phenyl | MeO | |
| 36 | 2-Cl-pyrid-4-yl | 3,4-di-F-phenyl | MeO | |
| 37 | 2-Cl-pyrid-4-yl | 3-F-phenyl | MeO | |
| 38 | 2-Cl-pyrid-4-yl | 3-Cl-4-F-phenyl | MeO | |
| 39 | 2-CF$_3$-pyrid-4-yl | 2-CF$_3$-pyrid-4-yl | MeO | |
| 40 | 2-CF$_3$-pyrid-4-yl | 3,4-di-F-phenyl | MeO | |

TABLE 1-continued

Compounds of formula

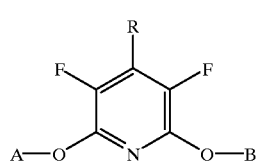

(Ia)

| Compound No. | A | B | R | m.p. [° C.] |
|---|---|---|---|---|
| 41 | 2-CF$_3$-pyrid-4-yl | 3-F-phenyl | MeO | |
| 42 | 2-CF$_3$-pyrid-4-yl | 3-CF$_3$-4-Cl-phenyl | MeO | |
| 43 | 2-CF$_3$-pyrid-4-yl | 3-Cl-4-F-phenyl | MeO | |
| 44 | 2-CF$_3$-pyrid-4-yl | 3-CF$_3$-4-F-phenyl | MeO | |
| 45 | 2-CF$_3$-pyrid-4-yl | 3,4-di-Cl-phenyl | MeO | |
| 46 | 2-CF$_3$-pyrid-4-yl | 3,5-di-F-phenyl | MeO | |
| 47 | 2-CF$_3$-pyrid-4-yl | 3-CF$_3$-phenyl | Me | |
| 48 | 2-CF$_3$-pyrid-4-yl | 3,4-di-F-phenyl | Me | |
| 49 | 2-CF$_3$-pyrid-4-yl | 3-F-phenyl | Me | |
| 50 | 2-CF$_3$-pyrid-4-yl | 3-Cl-4-F-phenyl | Me | |
| 51 | 2-CF$_3$-pyrid-4-yl | 2-CF$_3$-pyrid-4-yl | Me | |
| 52 | 2-CF$_3$-pyrid-4-yl | 2-CF$_3$-pyrid-4-yl | MeO | |
| 53 | 2-CF$_3$-pyrid-4-yl | 3-CF$_3$-phenyl | MeO | |
| 54 | 2-CF$_3$-pyrid-4-yl | 3,4-di-F-phenyl | MeO | |
| 55 | 2-CF$_3$-pyrid-4-yl | 3-F-phenyl | MeO | |
| 56 | 2-CF$_3$-pyrid-4-yl | 3-Cl-4-F-phenyl | MeO | |
| 57 | 2-CHF$_2$O-pyrid-4-yl | 2-CHF$_2$O-pyrid-4-yl | Me | |
| 58 | 2-CHF$_2$O-pyrid-4-yl | 3,4-di-F-phenyl | MeO | |
| 59 | 2-CHF$_2$O-pyrid-4-yl | 3-F-phenyl | MeO | |
| 60 | 2-CHF$_2$O-pyrid-4-yl | 3-CF$_3$-4-Cl-phenyl | MeO | |
| 61 | 2-CHF$_2$O-pyrid-4-yl | 3-Cl-4-F-phenyl | MeO | |
| 62 | 2-CHF$_2$O-pyrid-4-yl | 3-CF$_3$-4-F-phenyl | MeO | |
| 63 | 2-CHF$_2$O-pyrid-4-yl | 3,4-di-Cl-phenyl | MeO | |
| 64 | 2-CHF$_2$O-pyrid-4-yl | 3,5-di-F-phenyl | Me | |
| 65 | 2-CHF$_2$O-pyrid-4-yl | 3-CF$_3$-phenyl | Me | |
| 66 | 2-CHF$_2$O-pyrid-4-yl | 3,4-di-F-phenyl | Me | |
| 67 | 2-CHF$_2$O-pyrid-4-yl | 3-F-phenyl | Me | |
| 68 | 2-CHF$_2$O-pyrid-4-yl | 3-Cl-4-F-phenyl | Me | |
| 69 | 2-CHF$_2$O-pyrid-4-yl | 2-CHF$_2$O-pyrid-4-yl | MeO | |
| 70 | 2-CHF$_2$O-pyrid-4-yl | 3-CF$_3$-phenyl | MeO | |

TABLE 2

Compounds of formula

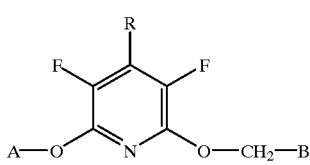

(Ib)

| Compound No. | A | B | R | m.p. [° C.] |
|---|---|---|---|---|
| 1 | 1-CH$_3$-3-CF$_3$-pyrazol-5-yl | 4-F-phenyl | MeO | oil |
| 2 | 1-CH$_3$-3-CF$_3$-pyrazol-5-yl | 4-F-phenyl | Me | oil |
| 3 | 1-CH$_3$-3-CF$_3$-pyrazol-5-yl | 2,4-di-F-phenyl | Me | oil |
| 4 | 1-CH$_3$-3-CF$_3$-pyrazol-5-yl | 3,4-di-F-phenyl | Me | oil |
| 5 | 1-CH$_3$-3-CF$_3$-pyrazol-5-yl | 2,4-di-F-phenyl | MeO | 94 |
| 6 | 1-CH$_3$-3-CF$_3$-pyrazol-5-yl | 3,4-di-F-phenyl | MeO | oil |
| 7 | 1-CH$_3$-3-CF$_3$-pyrazol-5-yl | phenyl | MeO | |
| 8 | 1-CH$_3$-3-CF$_3$-pyrazol-5-yl | phenyl | Me | |
| 9 | 1-CH$_3$-3-CF$_3$-pyrazol-5-yl | 3-F-phenyl | Me | |
| 10 | 1-CH$_3$-3-CF$_3$-pyrazol-5-yl | 3-F-phenyl | MeO | |
| 11 | 1-CH$_3$-3-CF$_3$-pyrazol-5-yl | 2,3,4-tri-F-phenyl | Me | |
| 12 | 1-CH$_3$-3-CF$_3$-pyrazol-5-yl | 2,3,4-tri-F-phenyl | MeO | |

TABLE 2-continued

Compounds of formula

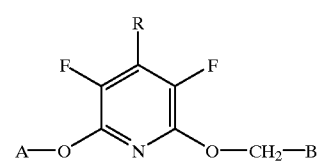

(Ib)

| Compound No. | A | B | R | m.p. [° C.] |
|---|---|---|---|---|
| 13 | 1-CH$_3$-3-CF$_3$-pyrazol-5-yl | thien-2-yl | Me | |
| 14 | 1-CH$_3$-3-CF$_3$-pyrazol-5-yl | thien-3-yl | MeO | |
| 15 | 1-CH$_3$-3-CF$_3$-pyrazol-5-yl | 5-F-thien-2-yl | Me | |
| 16 | 1-CH$_3$-3-CF$_3$-pyrazol-5-yl | 5-F-thien-3-yl | MeO | |
| 17 | 3-CF$_3$-phenyl | 4-F-phenyl | MeO | |
| 18 | 3-CF$_3$-phenyl | 4-F-phenyl | Me | |
| 19 | 3-CF$_3$-phenyl | 2,4-di-F-phenyl | Me | |
| 20 | 3-CF$_3$-phenyl | 3,4-di-F-phenyl | Me | |
| 21 | 3-CF$_3$-phenyl | 2,4-di-F-phenyl | MeO | |
| 22 | 3-CF$_3$-phenyl | 3,4-di-F-phenyl | MeO | |
| 23 | 3-CF$_3$-phenyl | phenyl | MeO | |
| 24 | 3-CF$_3$-phenyl | phenyl | Me | |

TABLE 2-continued

Compounds of formula (Ib)

$$\text{A—O}\underset{N}{\overset{R}{\diagdown\phantom{X}\diagup}}\text{O—CH}_2\text{—B}$$
(with F substituents at 3,5-positions)

| Compound No. | A | B | R | m.p. [°C.] |
|---|---|---|---|---|
| 25 | 3-CF$_3$-phenyl | 3-F-phenyl | Me | |
| 26 | 3-CF$_3$-phenyl | 3-F-phenyl | MeO | |
| 27 | 3-CF$_3$-phenyl | 2,3,4-tri-F-phenyl | Me | |
| 28 | 3-CF$_3$-phenyl | 2,3,4-tri-F-phenyl | MeO | |
| 29 | 3-CF$_3$-phenyl | thien-2-yl | Me | |
| 30 | 3-CF$_3$-phenyl | thien-3-yl | MeO | |
| 31 | 3-CF$_3$-phenyl | 5-F-thien-2-yl | Me | |
| 32 | 3-CF$_3$-phenyl | 5-F-thien-3-yl | MeO | |
| 33 | 3-CF$_3$-phenyl | 2-methylphenyl | Me | |
| 34 | 3-CF$_3$-phenyl | 2-methylphenyl | MeO | |
| 35 | 2-CF$_3$-pyrid-4-yl | 4-F-phenyl | MeO | |
| 36 | 2-CF$_3$-pyrid-4-yl | 4-F-phenyl | Me | |
| 37 | 2-CF$_3$-pyrid-4-yl | 2,4-di-F-phenyl | Me | |
| 38 | 2-CF$_3$-pyrid-4-yl | 3,4-di-F-phenyl | Me | |
| 39 | 2-CF$_3$-pyrid-4-yl | 2,4-di-F-phenyl | MeO | |
| 40 | 2-CF$_3$-pyrid-4-yl | 3,4-di-F-phenyl | MeO | |
| 41 | 2-CF$_3$-pyrid-4-yl | phenyl | MeO | |
| 42 | 2-CF$_3$-pyrid-4-yl | phenyl | Me | |
| 43 | 2-CF$_3$-pyrid-4-yl | 3-F-phenyl | Me | |
| 44 | 2-CF$_3$-pyrid-4-yl | 3-F-phenyl | MeO | |
| 45 | 2-CF$_3$-pyrid-4-yl | 2,3,4-tri-F-phenyl | Me | |
| 46 | 2-CF$_3$-pyrid-4-yl | 2,3,4-tri-F-phenyl | MeO | |
| 47 | 2-CF$_3$-pyrid-4-yl | thien-2-yl | Me | |
| 48 | 2-CF$_3$-pyrid-4-yl | thien-3-yl | MeO | |
| 49 | 2-CF$_3$-pyrid-4-yl | 5-F-thien-2-yl | Me | |
| 50 | 2-CF$_3$-pyrid-4-yl | 5-F-thien-3-yl | MeO | |
| 51 | 2-CF$_3$-pyrid-4-yl | 2-methylphenyl | Me | |
| 52 | 2-CF$_3$-pyrid-4-yl | 2-methylphenyl | MeO | |
| 53 | 2-CHF$_2$O-pyrid-4-yl | 4-F-phenyl | MeO | |
| 54 | 2-CHF$_2$O-pyrid-4-yl | 4-F-phenyl | Me | |
| 55 | 2-CHF$_2$O-pyrid-4-yl | 2,4-di-F-phenyl | Me | |
| 56 | 2-CHF$_2$O-pyrid-4-yl | 3,4-di-F-phenyl | Me | |
| 57 | 2-CHF$_2$O-pyrid-4-yl | 2,4-di-F-phenyl | MeO | |
| 58 | 2-CHF$_2$O-pyrid-4-yl | 3,4-di-F-phenyl | MeO | |
| 59 | 2-CHF$_2$O-pyrid-4-yl | phenyl | MeO | |
| 60 | 2-CHF$_2$O-pyrid-4-yl | phenyl | Me | |
| 61 | 2-CHF$_2$O-pyrid-4-yl | 3-F-phenyl | Me | |
| 62 | 2-CHF$_2$O-pyrid-4-yl | 3-F-phenyl | MeO | |
| 63 | 2-CHF$_2$O-pyrid-4-yl | 2,3,4-tri-F-phenyl | Me | |
| 64 | 2-CHF$_2$O-pyrid-4-yl | 2,3,4-tri-F-phenyl | MeO | |
| 65 | 2-CHF$_2$O-pyrid-4-yl | thien-2-yl | Me | |
| 66 | 2-CHF$_2$O-pyrid-4-yl | thien-3-yl | MeO | |
| 67 | 2-CHF$_2$O-pyrid-4-yl | 5-F-thien-2-yl | Me | |
| 68 | 2-CHF$_2$O-pyrid-4-yl | 5-F-thien-3-yl | MeO | |
| 69 | 2-CHF$_2$O-pyrid-4-yl | 2-methylphenyl | Me | |
| 70 | 2-CHF$_2$O-pyrid-4-yl | 2-methylphenyl | MeO | |
| 71 | 2-Cl-pyrid-4-yl | 4-F-phenyl | MeO | |
| 72 | 2-Cl-pyrid-4-yl | 4-F-phenyl | Me | |
| 73 | 2-Cl-pyrid-4-yl | 2,4-di-F-phenyl | Me | |
| 74 | 2-Cl-pyrid-4-yl | 3,4-di-F-phenyl | Me | |
| 75 | 2-Cl-pyrid-4-yl | 2,4-di-F-phenyl | MeO | |
| 76 | 2-Cl-pyrid-4-yl | 3,4-di-F-phenyl | MeO | |
| 77 | 2-Cl-pyrid-4-yl | phenyl | MeO | |
| 78 | 2-Cl-pyrid-4-yl | phenyl | Me | |
| 79 | 2-Cl-pyrid-4-yl | 3-F-phenyl | Me | |
| 80 | 2-Cl-pyrid-4-yl | 3-F-phenyl | MeO | |
| 81 | 2-Cl-pyrid-4-yl | 2,3,4-tri-F-phenyl | Me | |
| 82 | 2-Cl-pyrid-4-yl | 2,3,4-tri-F-phenyl | MeO | |
| 83 | 2-Cl-pyrid-4-yl | thien-2-yl | Me | |
| 84 | 2-Cl-pyrid-4-yl | thien-3-yl | MeO | |
| 85 | 2-Cl-pyrid-4-yl | 5-F-thien-2-yl | Me | |
| 86 | 2-Cl-pyrid-4-yl | 5-F-thien-3-yl | MeO | |
| 87 | 2-Cl-pyrid-4-yl | 2-methylphenyl | Me | |
| 88 | 2-Cl-pyrid-4-yl | 2-methylphenyl | MeO | |

EXAMPLE 6

Herbicidal Activity Tests

1. Pre-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting, the pots are sprayed with the selected aqueous acetone solution containing test compound in sufficient quantity to provide the equivalent of about 0.0125 to 0.1 kg per hectare of test compound per pot. The treated pots are then placed on greenhouse benches, watered and cared for in accordance with conventional greenhouse procedures. From 2 to 4 weeks after treatment, the tests are terminated and each pot is examined and rated according to the rating system set forth below.

| Rating System | % Difference in Growth Versus Untreated Control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |

| Plant Species Used | | |
|---|---|---|
| A = HORVW | Hordeum vulgare | winter barley |
| B = ZEAMX | Zea mays | maize |
| C = GLYMA | Glycine max | soyabeans |
| D = SETVI | Setaria viridis | green foxtail |
| E = ABUTH | Abutilon theophrasti | velvetlaef |
| F = IPOHE | Ipomoea hederacea | morning glory |
| G = MATIN | Matricaria inodora | mayweed |
| H = STEME | Stellaria media | chickweed |
| I = CHEAL | Chenopodium album | lambsquarters |
| J = AMBEL | Ambrosia artemiisifolia | ragweed |

The herbicidal proficiency of the active ingredients of the present invention is evident from the test results which are recorded in Tables A to D below.

Crop Selectivity and Weed Control of Compounds According to the Invention in Pre-emergence Application The compounds of the invention showed good selectivity in maize up to the highest dose of 100 g/ha, while the standard was only at the lower dose of 25 g/ha similarly selective in maize. Furthermore, the compounds of the present invention displayed good selectivity in soybeans, clearly better than that of the standard. At crop selective doses the compounds of the present invention showed superior weed control over the "standard" (4-methyl-2-(1-methyl-3-trifluoromethylpyrazol-5-yl-oxy)-6-benzyloxy-pyridine) described in WO 94/22833. The results are these tests as presented in Tables A and B below.

TABLE A

Crop selectivity and weed control of compounds according to the invention in pre-emergence application -- crop and weed species

| Compound | dose [kg/ha] | A | B | C | D | E | F | G | H | I | J |
|---|---|---|---|---|---|---|---|---|---|---|---|
| Example 4 | 0.100 | 4 | 1 | 2 | 9 | 6 | 9 | 9 | 9 | 9 | 9 |
|  | 0.025 | 3 | 1 | 2 | 6 | 3 | 4 | 9 | 7 | 9 | 6 |
|  | 0.0125 | 1 | 1 | 1 | 3 | 2 | 3 | 7 | 4 | 8 | 5 |
| Tab. 2/no. 1 | 0.100 | 4 | 1 | 3 | 9 | 9 | 5 | 9 | 9 | 8 | 8 |
|  | 0.025 | 3 | 1 | 2 | 9 | 9 | 4 | 9 | 8 | 8 | 8 |
|  | 0.0125 | 2 | 1 | 2 | 9 | 9 | 3 | 8 | 6 | 6 | 5 |
| Tab. 2/no. 6 | 0.100 | 4 | 2 | 3 | 9 | 9 | 4 | 9 | 8 | 7 | 9 |
|  | 0.025 | 2 | 1 | 2 | 9 | 9 | 2 | 9 | 7 | 7 | 9 |
|  | 0.0125 | 1 | 0 | 1 | 9 | 9 | 1 | 6 | 4 | 6 | 6 |
| Standard* | 0.100 | 4 | 4 | 4 | 9 | 9 | 7 | 9 | 9 | 8 | 9 |
|  | 0.025 | 3 | 2 | 4 | 9 | 9 | 7 | 9 | 9 | 8 | 8 |
|  | 0.0125 | 3 | 1 | 2 | 9 | 9 | 4 | 8 | 7 | 8 | 7 |

*Standard: (4-methyl-2-(1-methyl-3-trifluoromethylpyrazol-5-yl-oxy)-6-benzyloxy-pyridine)

The compounds of the invention were more selective in soybeans than the standard (see Table A). This was particularly the case for the compound of Example 2(Table 1 no. 1) and the compound no. 2 of Table 2. Furthermore, the compounds of the invention displayed excellent overall levels of weed control. This was demonstrated in particular for compound no. 3 of Table 2 showing superior activity over the standard against Setaria, Abutilon, Ipomoea and Stellaria.

TABLE B

Crop selectivity and weed control of compounds according to the invention in pre-emergence application -- crop and weed species

| Compound | dose [kg/ha] | A | B | C | D | E | F | G | H |
|---|---|---|---|---|---|---|---|---|---|
| Tab. 1/No. 1 | 0.100 | 5 | 5 | 4 | 9 | 9 | 9 | 9 | 9 |
|  | 0.025 | 4 | 4 | 1 | 9 | 8 | 5 | 8 | 9 |
|  | 0.0125 | 4 | 3 | 1 | 7 | 8 | 4 | 8 | 8 |
| Tab. 2/No. 2 | 0.100 | 5 | 3 | 2 | 9 | 8 | 6 | 9 | 8 |
|  | 0.025 | 4 | 2 | 1 | 9 | 5 | 4 | 9 | 7 |
|  | 0.0125 | 2 | 0 | 1 | 9 | 4 | 2 | 8 | 7 |
| Tab. 2/No .3 | 0.100 | 4 | 3 | 4 | 9 | 8 | 9 | 8 | 9 |
|  | 0.025 | 3 | 2 | 3 | 9 | 7 | 7 | 8 | 8 |
|  | 0.0125 | 2 | 2 | 2 | 8 | 6 | 5 | 8 | 7 |
| standard* | 0.100 | 4 | 4 | 4 | 9 | 8 | 9 | 9 | 8 |
|  | 0.025 | 3 | 2 | 4 | 9 | 6 | 5 | 9 | 6 |
|  | 0.0125 | 3 | 1 | 2 | 4 | 5 | 5 | 8 | 5 |

*Standard: (4-methyl-2-(1-methyl-3-trifluoromethylpyrazol-5-yl-oxy)-6-benzyloxy-pyridine)

2. Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels equivalent of about 0.0125 to 0.1 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided above. A rating 0 indicates growth as untreated control, a rating 9 indicates death. The results of the test are set out in Tables C and D below.

Crop Selectivity and Weed Control of Compounds According to the Invention in Post-emergence Application In post-emergence application the compounds of the invention are very selective in maize up to 25 g/ha, displaying good overall levels of performance against weeds. In barley the compounds of the invention, in particular compound no.1 in TABLE 2, are effective for both grass control such as Setaria virides and broad-leaved weed control at crop selective doses.

TABLE C

Crop selectivity and weed control of compounds according to the invention in post-emergence application -- crop and weed species

| Compound | dose [kg/ha] | A | B | D | E | F | G | I | J |
|---|---|---|---|---|---|---|---|---|---|
| Example 4 | 0.100 | 3 | 3 | 7 | 9 | 9 | 7 | 8 | 5 |
|  | 0.025 | 3 | 2 | 6 | 8 | 9 | 6 | 8 | 4 |
|  | 0.0125 | 2 | 2 | 4 | 6 | 8 | 5 | 7 | 4 |
| Tab. 2/no. 1 | 0.100 | 4 | 3 | 9 | 9 | 9 | 8 | 8 | 5 |
|  | 0.025 | 2 | 2 | 8 | 8 | 9 | 6 | 8 | 4 |
|  | 0.0125 | 2 | 1 | 6 | 6 | 8 | 5 | 8 | 4 |
| Tab. 2/no. 6 | 0.100 | 4 | 3 | 9 | 9 | 9 | 8 | 8 | 6 |
|  | 0.025 | 3 | 2 | 9 | 9 | 8 | 7 | 8 | 4 |
|  | 0.0125 | 2 | 1 | 5 | 7 | 8 | 6 | 8 | 3 |

The compounds of the invention have good herbicidal activity on grasses such as Setaria and broad-leaved weeds. In particular compound no. 1 of Table 1 and no.2 of Table 2 demonstrated superior weed control over the standard (see above). Compound no.1 of TABLE 1 displayed furthermore clearly better selectivity in soybeans and maize than the standard.

TABLE D

Crop selectivity and weed control of compounds according to the invention in post-emergence application -- crop and weed species

| Compound | dose [kg/ha] | A | B | C | D | E | F | G | H |
|---|---|---|---|---|---|---|---|---|---|
| Tab. 1/no. 1 | 0.100 | 3 | 3 | 5 | 8 | 9 | 8 | 8 | 4 |
|  | 0.025 | 3 | 2 | 3 | 8 | 9 | 7 | 7 | 4 |
|  | 0.0125 | 2 | 2 | 2 | 7 | 8 | 6 | 5 | 3 |
| Tab. 2/no. 2 | 0.100 | 4 | 3 | 8 | 9 | 9 | 9 | 8 | 7 |
|  | 0.025 | 2 | 2 | 7 | 8 | 8 | 9 | 7 | 5 |
|  | 0.0125 | 2 | 2 | 6 | 7 | 8 | 8 | 7 | 4 |
| Tab. 2/no. 3 | 0.100 | 4 | 4 | 8 | 9 | 7 | 9 | 8 | 9 |
|  | 0.025 | 4 | 3 | 5 | 9 | 7 | 9 | 7 | 8 |
|  | 0.0125 | 3 | 2 | 4 | 7 | 6 | 9 | 7 | 8 |
| Tab. 2/no. 4 | 0.100 | 5 | 4 | 7 | 9 | 7 | 9 | 8 | 9 |
|  | 0.025 | 3 | 4 | 7 | 9 | 7 | 9 | 7 | 9 |
|  | 0.0125 | 3 | 3 | 5 | 8 | — | 9 | 7 | 9 |
| standard* | 0.100 | 4 | 4 | 8 | 7 | 9 | 9 | 7 | 6 |
|  | 0.025 | 3 | 3 | 7 | 6 | 9 | 9 | 6 | 4 |
|  | 0.0125 | 2 | 2 | 7 | 5 | 7 | 7 | 5 | 3 |

*Standard: (4-methyl-2-(1-methyl-3-trifluoromethylpyrazol-5-yl-oxy)-6-benzyloxy-pyridine)

What is claimed is:

1. A compound of formula I:

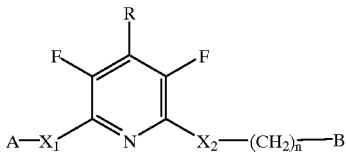

(I)

wherein

A represents an optionally substituted pyrazyl ring optionally substituted phenyl or naphthyl group said optional substituents being selected from the group consisting of halogen, nitro, cyano, amino, hydroxyl, $C_{1-4}$ alkyl, $C_{1-4}$ alkoxy, $C_{1-4}$ haloalkyl, $C_{1-4}$ haloalkylthio, $C_{1-4}$ haloalkoxy, $C_{2-4}$ A haloalkenyl, and halosulfanyl having up to 5 halogen atoms;

B represents an optionally substituted phenyl or naphthyl group said optional substituents being selected from the group consisting of halogen, nitro, cyano, amino, hydroxyl, $C_{1-4}$ alkyl, $C_{1-4}$ alkoxy, $C_{1-4}$ haloalkyl, $C_{1-4}$ haloalkylthio, $C_{1-4}$ haloalkoxy, $C_{2-4}$ A haloalkenyl, and halosulfanyl having up to 5 halogen atoms;

n represents an integer from 0 to 2;

R represents a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino or alkoxyamino group or a formamidino or cyano group;

$X_1$ and $X_2$ independently represent an oxygen or sulphur atom.

2. A compound as claimed in claim 1, wherein A is a group of formula

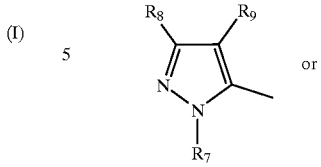

(a)

wherein $R_9$ is hydrogen, fluoro or chloro; $R_7$ is $C_{1-3}$ alkyl; and $R_8$ is $C_{1-4}$ alkyl, $C_{1-3}$ haloalkyl, a halogen atom, $C_{1-3}$ haloalkylthio or $C_{1-3}$ haloalkoxy.

3. A compound as claimed in claim 2, wherein B represents a optionally substituted phenyl or a 1–5 fold substituted phenyl group, wherein the substituents independently are $C_{1-4}$ alkyl, $C_{1-4}$ haloalkyl, $C_{1-4}$ alkoxy, $C_{1-4}$ haloalkoxy, cyano or $SF_5$ groups or halogen atoms.

4. A compound as claimed in claim 1 wherein R is a hydrogen, fluorine, bromine or chlorine atom or a methyl, ethyl, methoxy, methylthio, cyano or methylamino group.

5. A compound as claimed in claim 1 wherein n is 0 or 1.

6. A compound as claimed in claim 5 wherein A is 1-methyl-3-trifluoromethylpyrazol-5-yl, $X_1$ and $X_2$ are oxygen atoms and B is phenyl, fluorophenyl, 2-methylphenyl.

7. A herbicidal composition comprising as active ingredient a compound as claimed in claim 1, and a carrier.

8. A herbicidal composition comprising a compound as claimed in claim 6, and a carrier.

9. A method for combating undesired plants, which method comprises treating a locus with a herbicidally effective amount of a compound as claimed in claim 1.

10. A method for selectively combating undesired plants in maize or rice which comprises contacting said undesired plants with a herbicidally effective amount of a compound as claimed in claim 1.

* * * * *